(12) United States Patent
Vizulis et al.

(10) Patent No.: US 11,229,501 B2
(45) Date of Patent: Jan. 25, 2022

(54) NEGATIVE PRESSURE CHAMBER FOR PATIENT INTUBATION

(71) Applicant: V2 Engineering Group LLC, Ada, MI (US)

(72) Inventors: Karlis Vizulis, Ada, MI (US); James Edward Smith, Jr., West Olive, MI (US)

(73) Assignee: V2 Engineering Group LLC, Ada, MI (US)

( * ) Notice: Subject to any disclaimer, the term of this patent is extended or adjusted under 35 U.S.C. 154(b) by 0 days.

(21) Appl. No.: 17/220,690

(22) Filed: Apr. 1, 2021

(65) Prior Publication Data

US 2021/0307872 A1 Oct. 7, 2021

Related U.S. Application Data

(60) Provisional application No. 63/004,384, filed on Apr. 2, 2020, provisional application No. 63/034,330, filed on Jun. 3, 2020.

(51) Int. Cl.
*A61B 90/40* (2016.01)
*A61G 10/00* (2006.01)
*A61G 13/10* (2006.01)
*A61M 16/04* (2006.01)

(52) U.S. Cl.
CPC ............ *A61B 90/40* (2016.02); *A61G 10/005* (2013.01); *A61G 13/108* (2013.01); *A61B 2090/401* (2016.02); *A61M 16/0488* (2013.01)

(58) Field of Classification Search
CPC .............. A61B 90/40; A61B 2090/401; A61G 10/005; A61G 10/02; A61G 10/023; A61G 13/108; A61G 10/04; A61M 1/90; A61M 16/0488
See application file for complete search history.

(56) References Cited

U.S. PATENT DOCUMENTS

| | | | |
|---|---|---|---|
| 3,850,172 A | 11/1974 | Cazalis | |
| 4,550,713 A | 11/1985 | Hyman | |
| 4,583,758 A * | 4/1986 | Runion | ................. A61G 5/006 280/644 |
| 4,936,318 A | 6/1990 | Schoolman | |
| 4,949,714 A | 8/1990 | Orr | |
| 5,083,558 A | 1/1992 | Thomas et al. | |

(Continued)

FOREIGN PATENT DOCUMENTS

CN 201404402 2/2010

*Primary Examiner* — Keri J Nelson
(74) *Attorney, Agent, or Firm* — Kohn and Associates, PLLC

(57) ABSTRACT

A chamber for placement over a patient while allowing medical personnel to perform various medical procedures releasing virus, bacteria, or other contaminants, such as tracheal intubation, on the patient, including a frame forming and supporting two sidewalls and a curved center portion extending between the sidewalls of a transparent body, wherein the body includes at least one access hole, and wherein the chamber surrounds the patient's head and one of the sidewalls deforms around the patient's body in order to capture and exhaust any of the virus, bacteria, or other contaminants released by the patient during the medical procedure. A method of using the chamber of to perform a medical procedure on a patient releasing virus, bacteria, or other contaminants.

20 Claims, 21 Drawing Sheets

(56) References Cited

U.S. PATENT DOCUMENTS

| | | | |
|---|---|---|---|
| 5,498,130 A * | 3/1996 | Wakley | B60H 1/00457 |
| | | | 415/121.2 |
| 5,728,041 A | 3/1998 | Fowler, Jr. | |
| 6,685,622 B2 * | 2/2004 | O'Connor | A61B 90/40 |
| | | | 312/1 |
| 6,916,238 B2 | 7/2005 | Korman | |
| 7,503,890 B2 * | 3/2009 | Kubicsko | B08B 15/026 |
| | | | 600/21 |
| 8,298,130 B2 | 10/2012 | Maloney | |
| 9,310,088 B2 | 4/2016 | Melikov et al. | |
| 10,251,801 B2 | 4/2019 | Breegi et al. | |
| 2004/0255937 A1 | 12/2004 | Sun | |
| 2005/0085686 A1 | 4/2005 | Yuen | |
| 2005/0278838 A1 * | 12/2005 | Shenosky | A61G 10/005 |
| | | | 2/457 |
| 2016/0136024 A1 * | 5/2016 | Poenisch | A61J 15/0003 |
| | | | 600/21 |
| 2020/0179219 A1 * | 6/2020 | Petersen | A61G 10/02 |

* cited by examiner

NEGATIVE PRESSURE CHAMBER FOR PATIENT INTUBATION

BACKGROUND OF THE INVENTION

1. Technical Field

The present invention relates generally to a negative pressure chamber that can be used to protect a practitioner during procedures releasing virus, bacteria, or other contaminants from a patient, such as tracheal intubation of a patient, wherein the chamber is configured to be easily transported between patient beds.

2. Background Art

The coronavirus disease 19 (COVID-19) has been determined to be responsible for an outbreak of potentially fatal atypical pneumonia. This novel COVID-19, termed severe acute respiratory syndrome (SARS)-CoV-2, was found to be similar to the particular coronavirus that was responsible for the SARS pandemic that occurred in 2002.

The coronaviruses, Coronaviridae, are a large family of enveloped, non-segmented, positive-sense, single-stranded RNA viruses that infect a broad range of vertebrates. They are found in many birds and mammals, especially in bats. In humans, most coronaviruses tend to cause mild to moderate upper respiratory tract infections such as the common cold. However, some strains of coronaviruses can exhibit stronger virulence and can be quickly passed from human to human. In some cases, the infection is mild but in others the response can be severe. In extreme cases, death occurs due to gradual respiratory failure as the result of alveolar damage by the virus.

The coronavirus known as COVID-19 has been found to be highly contagious and is believed to be spread through droplets expelled into the air by a sick patient. The highly infectious nature and ease of spreading between humans has increased the number of patients sick COVID-19 at such a rate, they have been overwhelming the hospitals to the point that there is not enough protective gear to adequately protect the medical personnel (including doctors, nurses, physician assistants, and various people serving in emergency medical services, including firefighters, paramedics, and the like). As such, many medical personnel are being unnecessarily and dangerously exposed to COVID-19.

One of the times of highest exposure for medical personnel is when they perform tracheal intubation of a patient, which is the placement of a flexible plastic tube into the trachea to maintain an open airway or assist a patient with breathing. As is well known almost all critical patients of COVID-19 may need ventilators and most of those will be intubated at some point in time to facilitate ventilation of the lungs. The most widely used method of intubation is orotracheal, in which an endotracheal tube is passed through the mouth and vocal apparatus into the trachea. It is during this process that the medical personnel get close to the patient, and droplets may be expelled from the patient. Therefore, the very act of trying to save the patient through ventilation may create a very high risk of exposure to the medical personnel, and given the current lack of protective gear, the protective gear while protecting the medical personnel, if reused as currently suggested in some medical settings, may expose subsequent patients to COVID-19.

Other professionals work with either people or bodies in performing procedures that could release viruses or other undesired substances into the air. For example, dental hygienists or dentists can aspirate particles from a person's mouth into the air when performing a cleaning or dental procedure. Coroners performing work on a corpse may cause undesired particles to enter the air.

It is desirable to provide a safe way to intubate or perform medical procedures on patients that could release infectious agents, such as COVID-19 patients, which is not dependent solely on the protective gear of the medical personnel, such as mask, glasses, and gloves alone.

SUMMARY OF THE INVENTION

The present invention provides for a chamber for placement over a patient while allowing medical personnel to perform various medical procedures releasing virus, bacteria, or other contaminants, such as tracheal intubation, on the patient, including a frame forming and supporting two sidewalls and a curved center portion extending between the sidewalls of a transparent body, wherein the body includes at least one access hole, and wherein the chamber surrounds the patient's head and one of the sidewalls deforms around the patient's body in order to capture and exhaust any of the virus, bacteria, or other contaminants released by the patient during the medical procedure through negative pressure.

The present invention provides for a method of using a chamber of to perform a medical procedure on a patient releasing virus, bacteria, or other contaminants, by placing a chamber over a patient's head on a bed, wherein the chamber includes a frame forming and supporting two sidewalls and a curved center portion extending between the sidewalls of a transparent body, wherein the body includes at least one access hole, and wherein the one of the sidewalls deforms around the patient's body, providing negative pressure within the chamber, and medical personnel providing intubation to the patient through the at least one access hole in the body of the chamber while capturing and exhausting any of the virus, bacteria, or other contaminants released by the patient during the medical procedure.

DESCRIPTION OF THE DRAWINGS

Other advantages of the present invention are readily appreciated as the same becomes better understood by reference to the following detailed description when considered in connection with the accompanying drawings wherein.

DETAILED DESCRIPTION OF THE INVENTION

Figure 1:
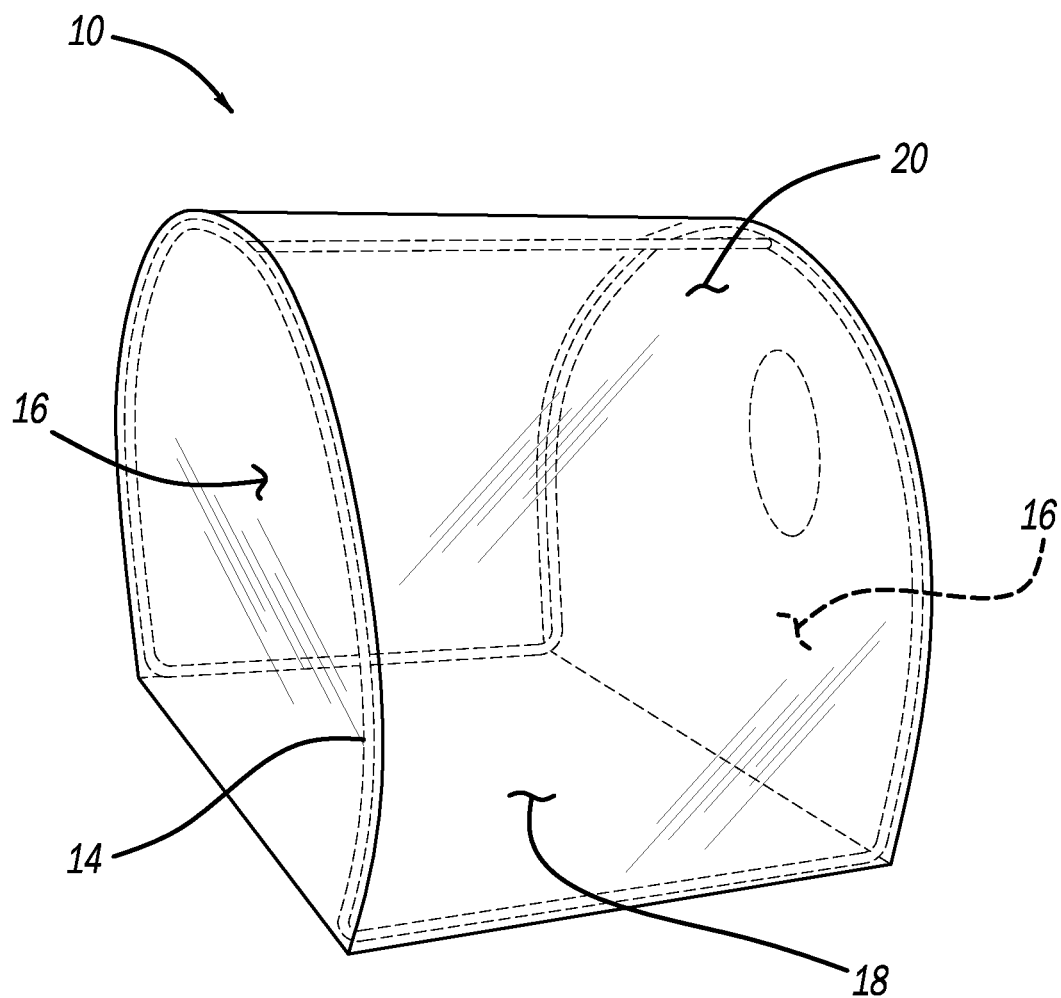
FIG. 1 is a picture of the chamber without the sealing engagements installed.

The present invention provides a chamber or shield, shown at 10 in the FIGURES, for placement over a patient 12, while still allowing medical personnel to perform various medical procedures on the patient 12 releasing virus, bacteria, or other contaminants (such as tracheal intubation of the patient 12). More specifically, the chamber 10 includes a frame 14 defining, supporting, and forming two sidewalls 16 and a curved center portion 18 extending between the sidewalls 16 of a transparent body 20. Essentially, the body 20 is in the shape of the frame 14 (i.e., the body 20 forms the shape of the two sidewalls 16 and curved center portion 18), shown in FIGS. 1-4. The chamber 10 surrounds the patient's head 22 and one of the sidewalls 16 deforms around the patient's body in order to capture and exhaust any of the virus, bacteria, or other contaminants released by the patient 12 during the medical procedure through negative pressure.

Figure 2:
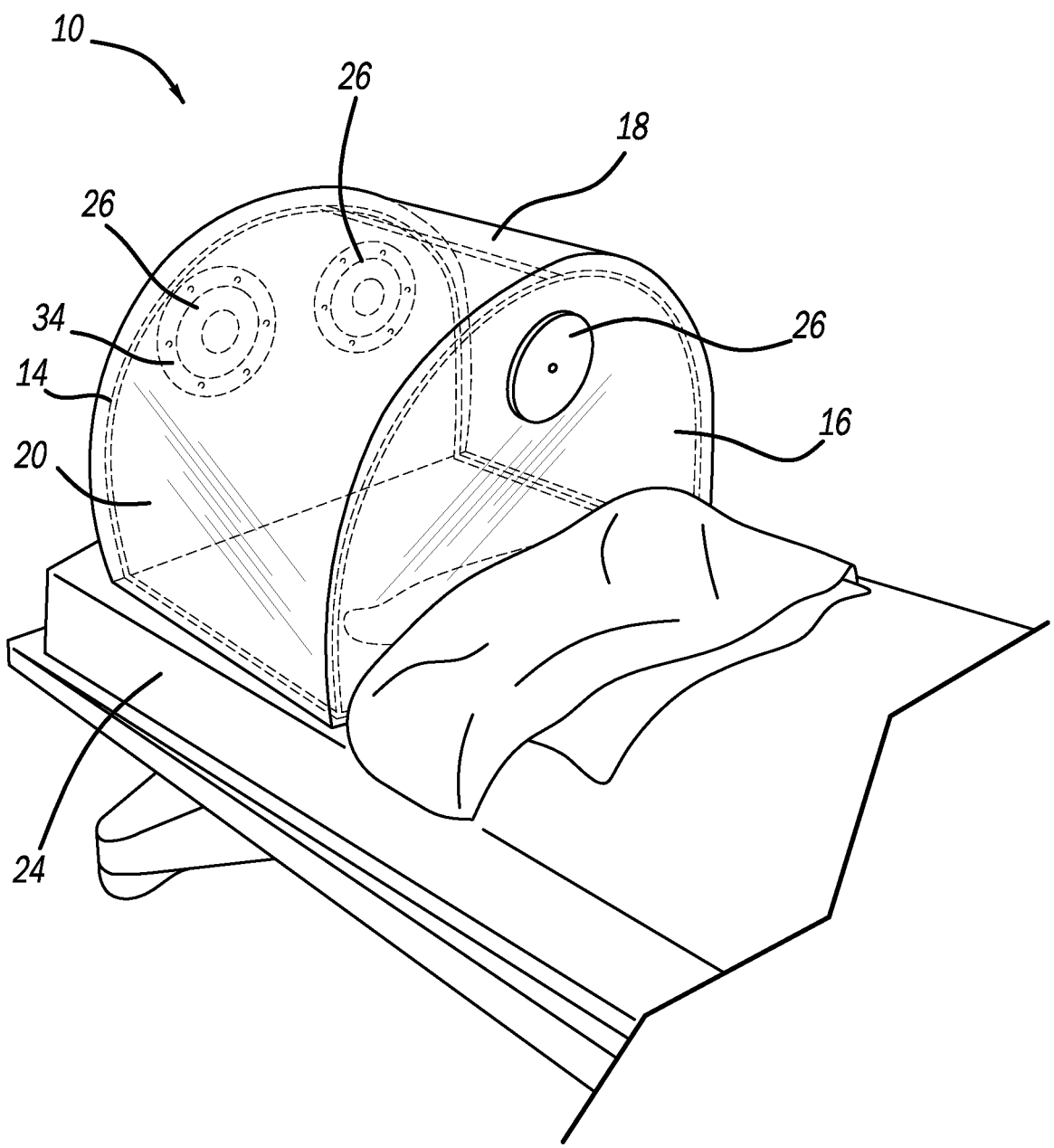
FIG. 2 is a front left perspective picture of the chamber.
Figure 3:
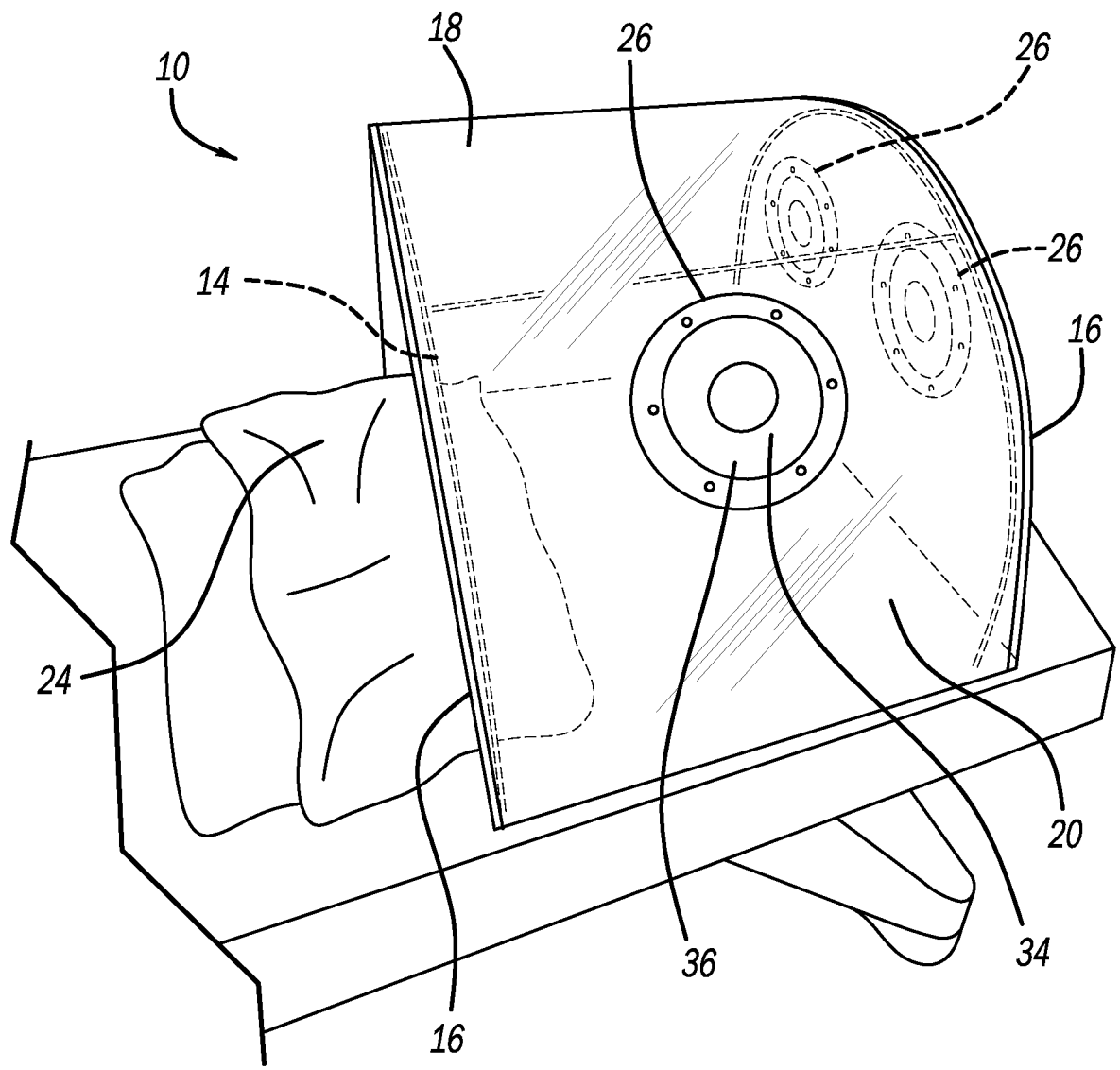
FIG. 3 is a right side perspective picture of the chamber.

The chamber 10 can be formed in a variety of sizes shapes and configurations, but in general is sized to fit over a patient's head 22 and leave enough room for medical personnel to easily and efficiently intubate or perform another medical procedure on the patient 12 without interference from body 20 of the chamber 10. The chamber 10 can also be sized in different sizes (smaller or larger) for different medical procedures. In addition, the chamber 10 is preferably sized to fit on but not extend past the sides of the typical hospital or medical office bed 24. The shape of the chamber 10 is exemplary and additional pieces can be used or a rectangle shape having multiple center pieces can be used. It is desirable that the chamber 10 be formed from a lightweight material yet have enough structural rigidity to substantially hold its shape and not collapse when placed under negative pressure. As shown in FIGS. 2 and 3, the chamber 10 is easily portable and can be moved from patient 12 to patient 12.

The chamber 10 can be made in multiple sizes to fit the smallest kids up through the largest adults; however, it is expected that it also could be sized to standard hospital size beds 24, such as the new standard 28" beds, or the older ER beds with a 26 inch base or 22 inch base for use in endoscopy or even a 20 inch base for operating room use. It is expected that to ensure a fit and allow for tolerance issues that the chamber 10 can be sized slightly smaller than the beds 24 on which it is used, but of course, a hospital can order a 26 inch base or even a 22 inch base for all chambers 10, which allows the chamber 10 to be used across the hospital on almost every size bed 24. Smaller versions could also be used in field hospitals easily.

The frame 14 can be made of any suitable lightweight material, such as plastic or metal. The frame 14 can be a single piece or multiple pieces connectable together for ease of transport and set up. The frame 14 can be assembled and the overlapping arched frame members can be assembled together with a bungee cord or other spring mechanism in the hollow center of the frame rods, similar to assembling tent poles, which allows for easier packaging of the chamber in a smaller package, as well as easy assembly.

Figure 6:
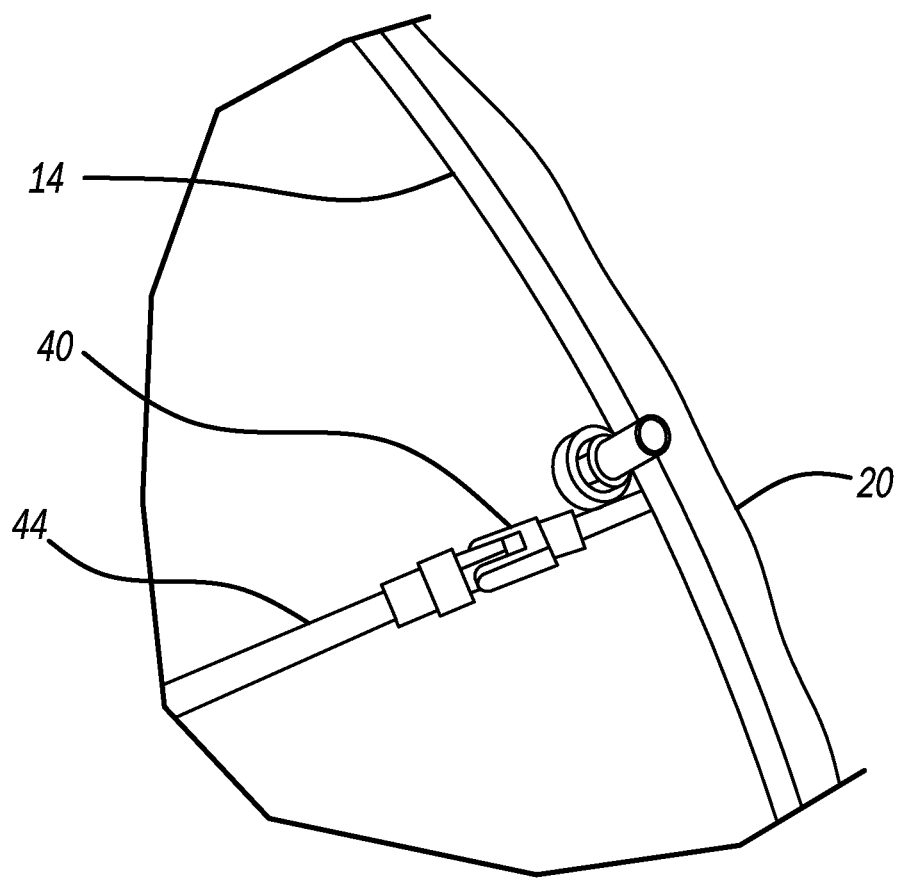
FIG. 6 is a perspective view of a hinge on a cross-member.
Figure 7:
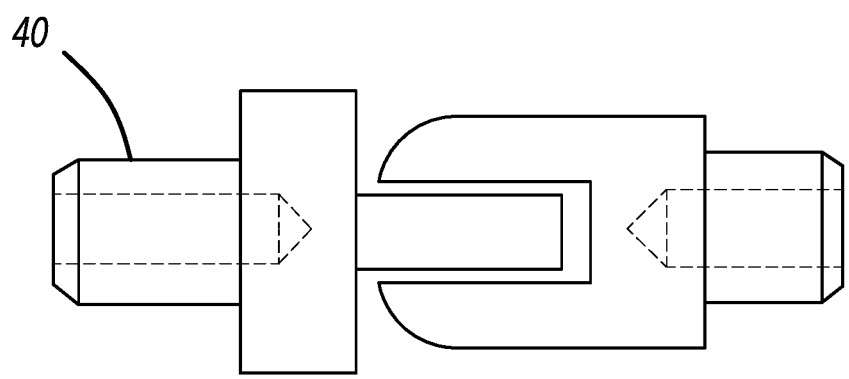
FIG. 7 shows example dimensions of a hinge.
Figure 8:
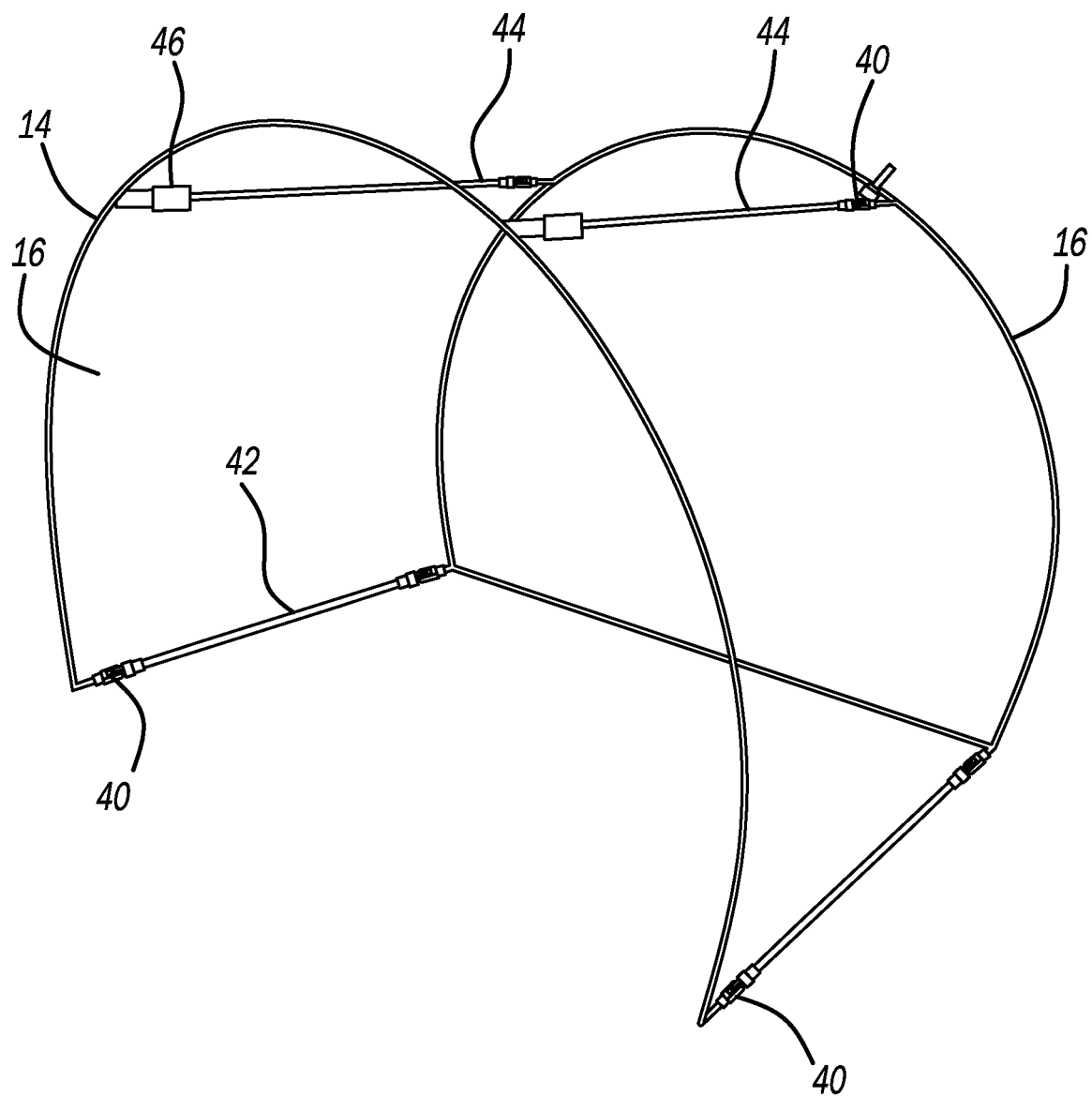
FIG. 8 is a side perspective view of a frame with hinges and cross-members.
Figure 9:
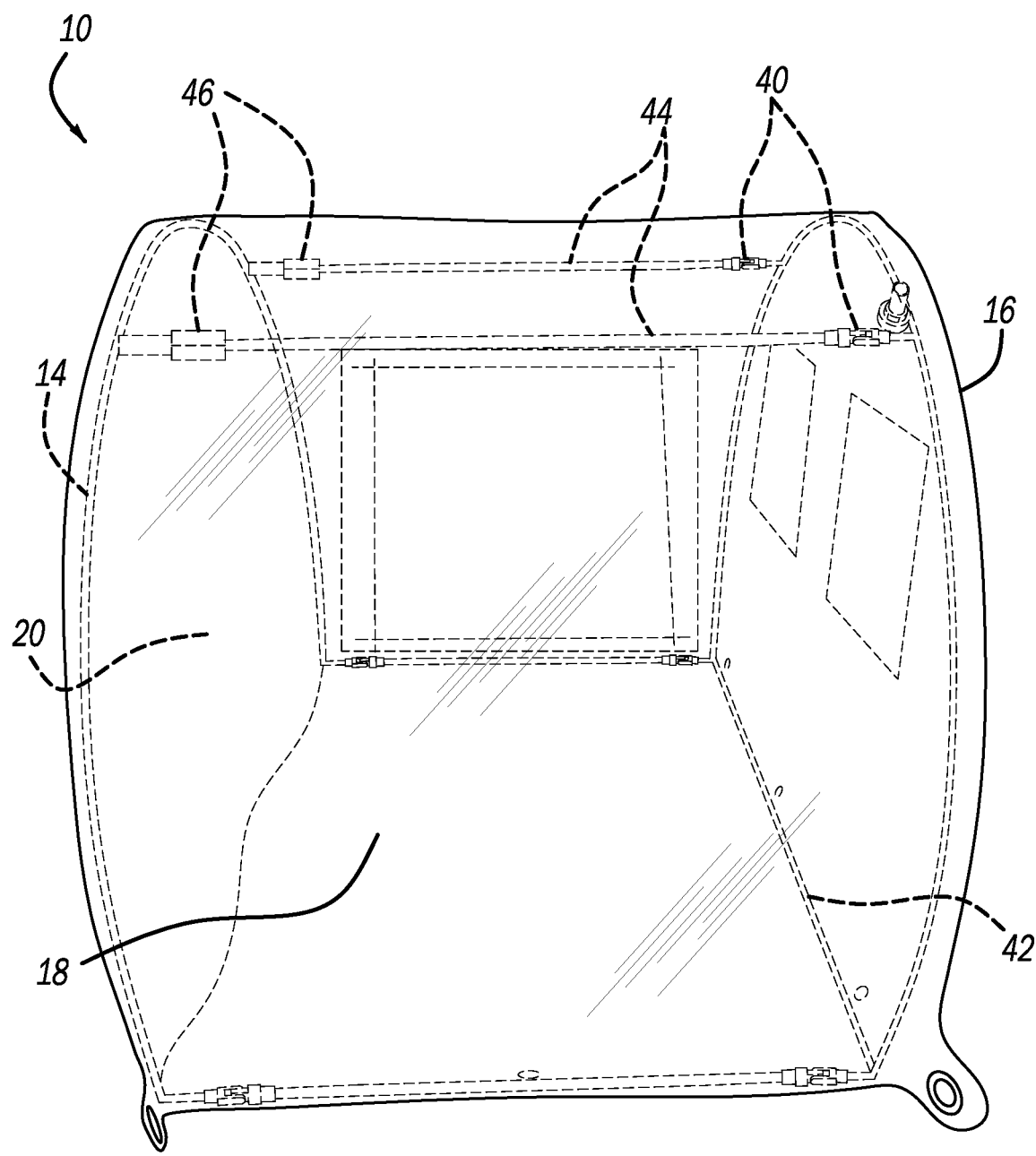
FIG. 9 is a side view of the chamber with cross-members.
Figure 10:
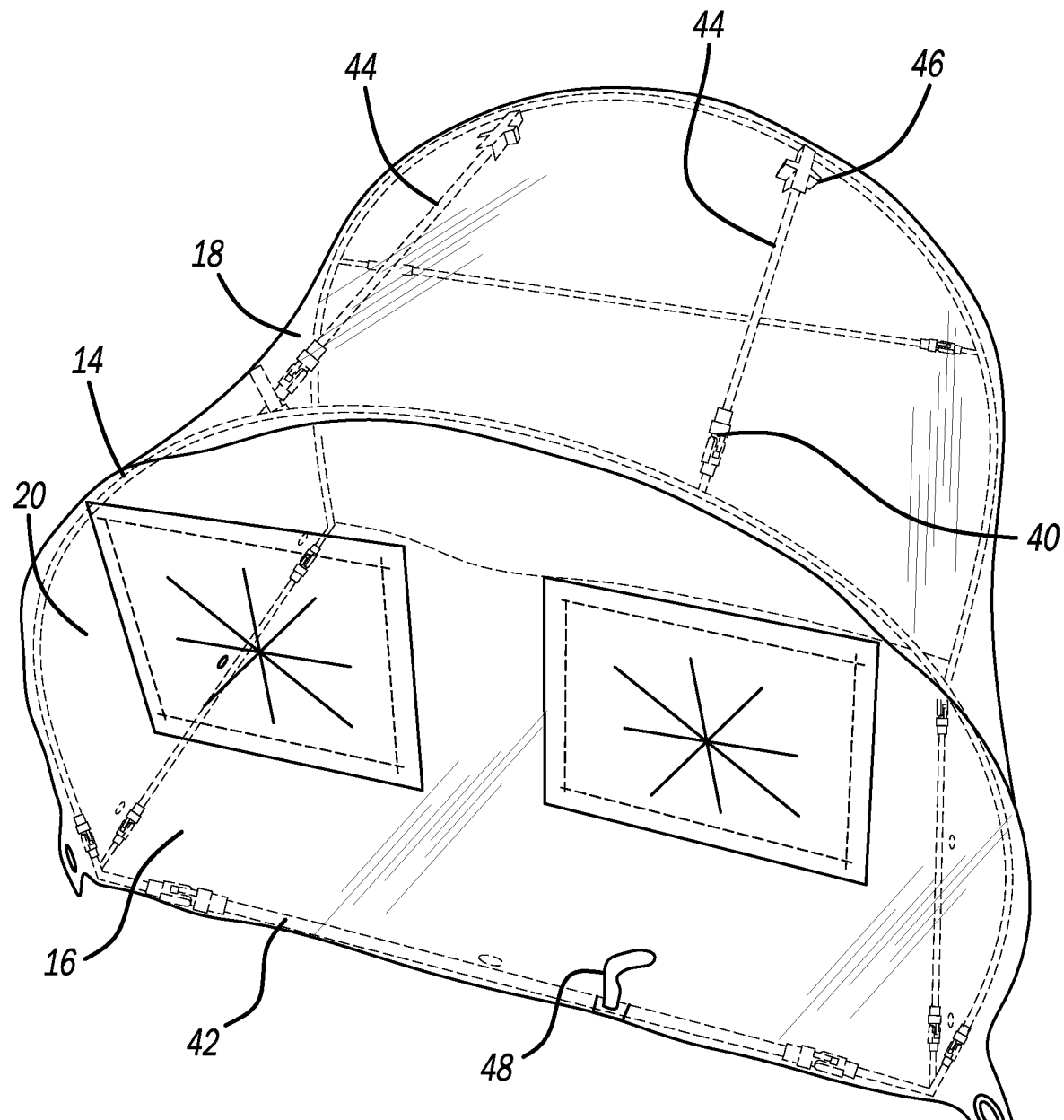
FIG. 10 is a back perspective view of the chamber with cross-members.
Figure 11:
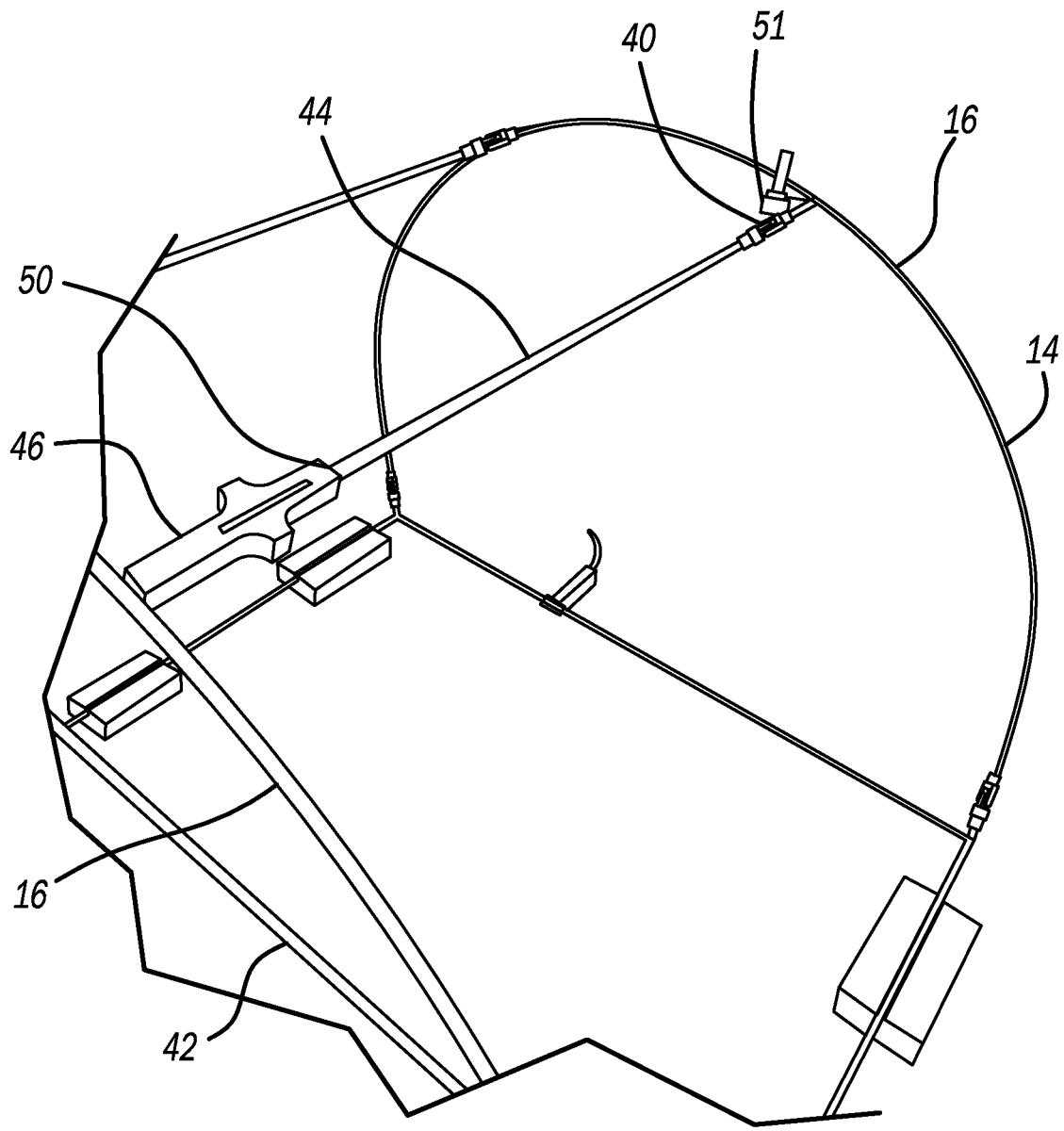
FIG. 11 is a top perspective view of a cross-member and frame.
Figure 12:
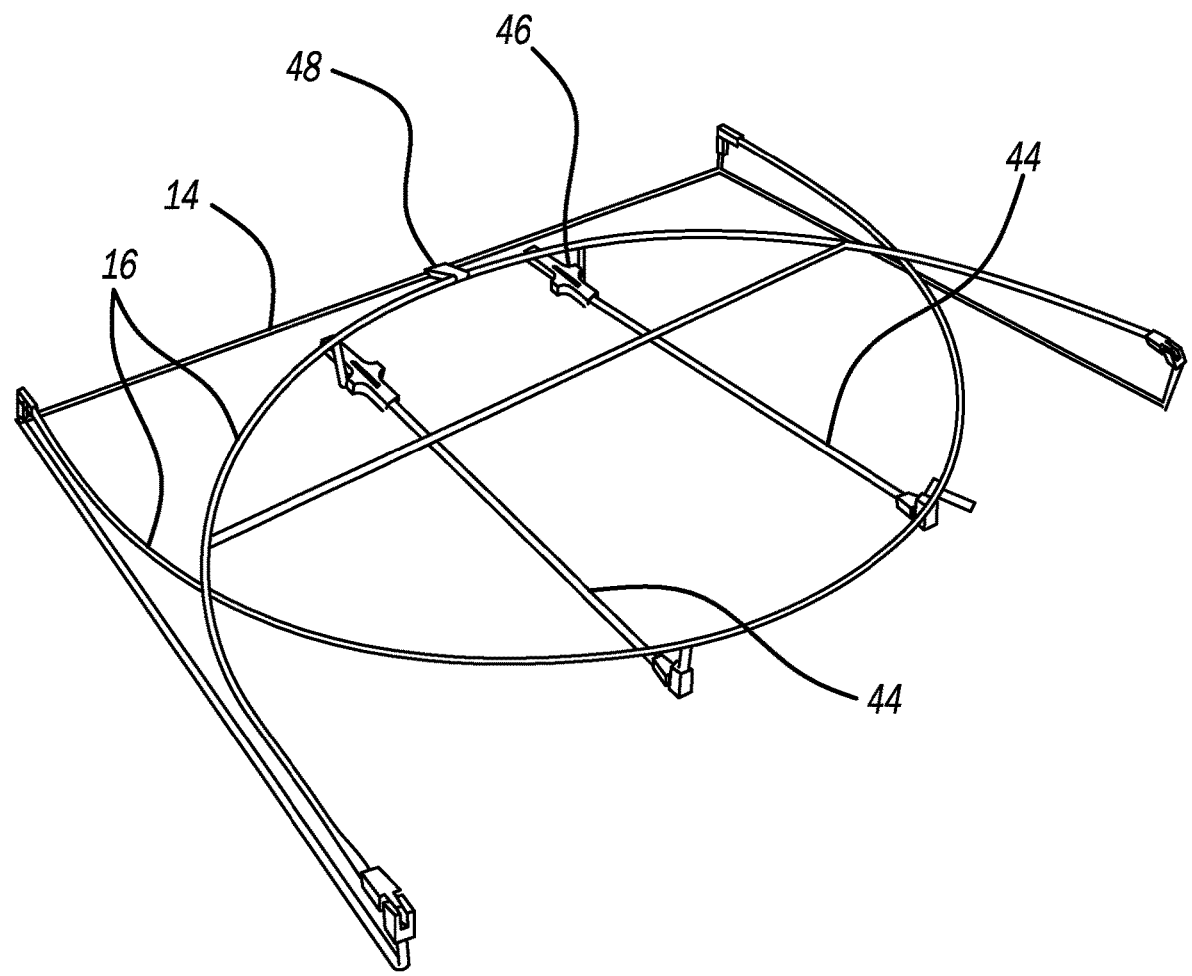
FIG. 12 is a top perspective view of a folded frame.
Figure 13A:
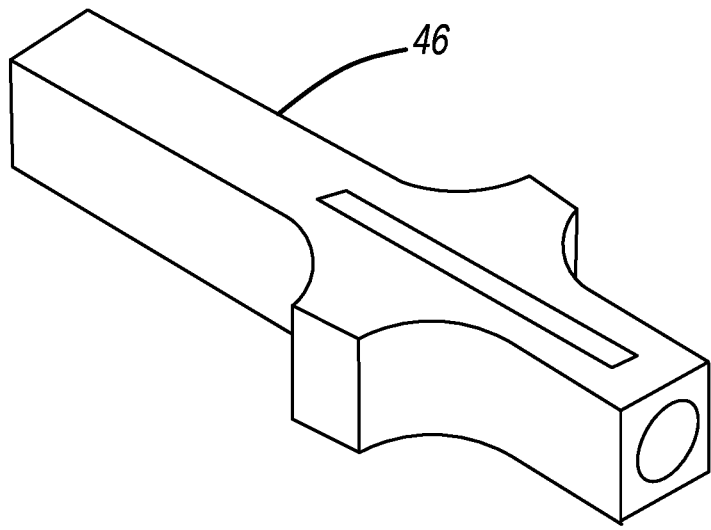
FIG. 13A is a top perspective view of a cross-member pressure sleeve.
Figure 13B:
FIG. 13B is a side view of a cross-member pressure sleeve.
Figure 13C:
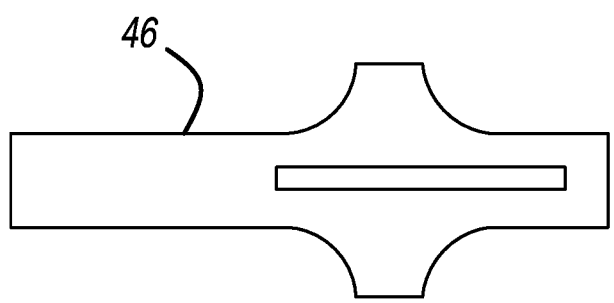
FIG. 13C is a top view of a cross-member pressure sleeve.
Figure 13D:
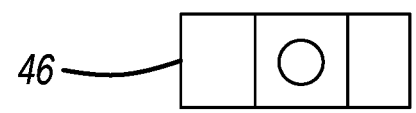
FIG. 13D is a front view of a cross-member pressure sleeve.
Figure 13E:
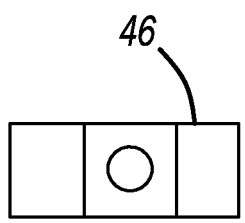
FIG. 13E is a back view of a cross-member pressure sleeve.
Figure 14:
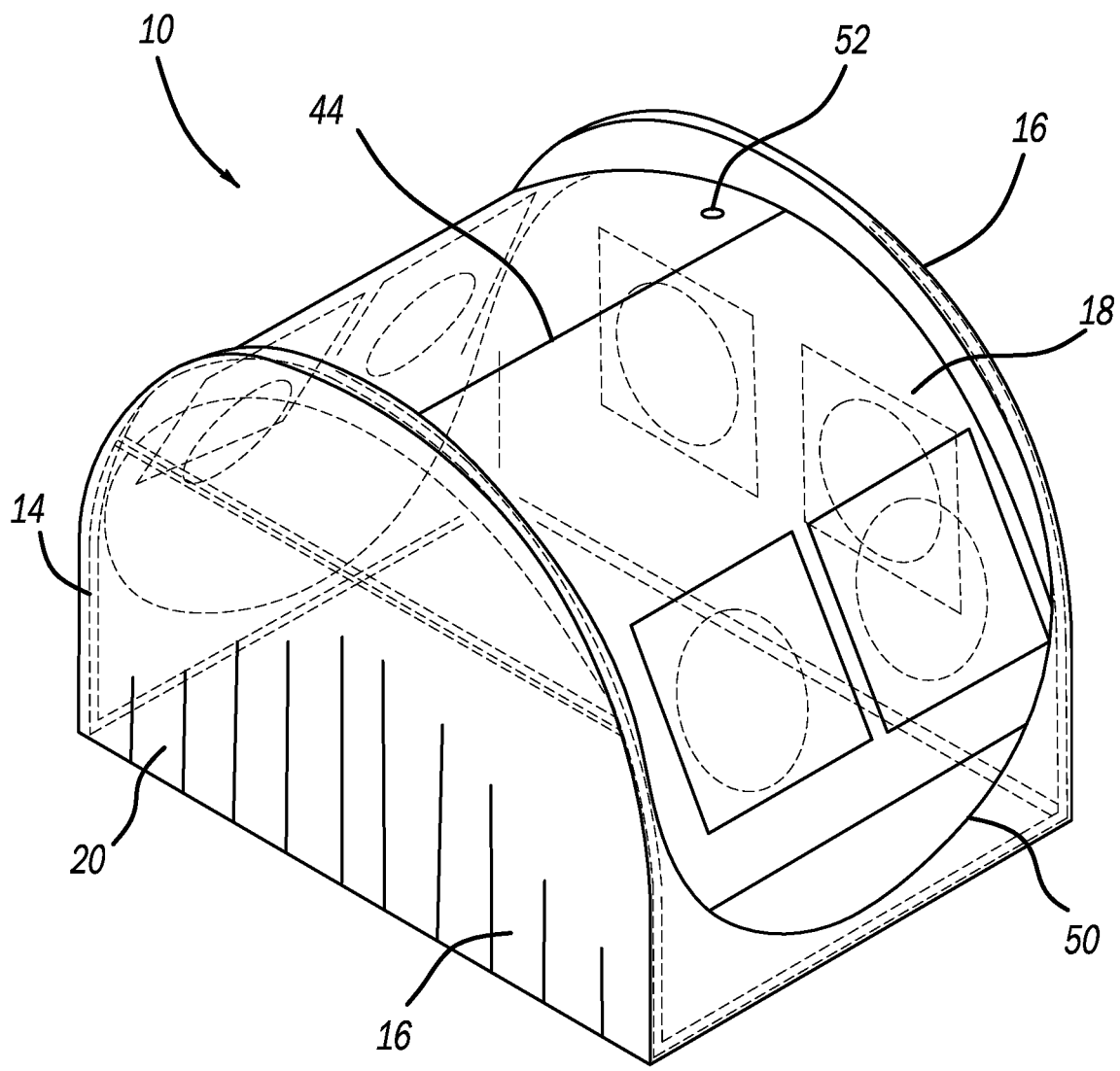
FIG. 14 is a side perspective view of a chamber assembled with zippers.

The frame 14 can include at least one hinge 40 that allows the frame 14 to be folded into a compact design for storage and/or shipping without damage, shown in FIGS. 6-13E. Example frame 14 dimensions are 28" long×20.5" wide×21" high. Using the hinged design, the frame 14 folds down from 21" high to 2.5" high. Hinges 40 can be included along a base 42 and/or at least one cross-member 44 that connects the two sidewalls 16 (shown in FIG. 8). FIG. 6 shows a hinge 40 on a cross-member 44. FIG. 7 shows example dimensions of a hinge 40. FIGS. 9 and 10 show the body 20 draped over the frame 14. Cross-members 44 can be releasably secured at a first end 50 to one sidewall 16 with pressure sleeve 46, shown in FIGS. 11 and 13A-13E, and have a second end 51 including a hinge 40. The pressure sleeve 46 can be pressed to release the cross-member 44 so that the frame 14 can be folded. FIG. 12 shows the frame 14 in a folded state.

A securing mechanism 48 such as a clip, hook and loop, or other suitable mechanism can be used to secure the frame 14 after folding so that it remains folded when carrying. The securing mechanism 48 can be located at any suitable place on the frame 14.

To assemble the chamber 10 with the hinged frame 14, the frame 14 is set down flat. Any securing mechanism 48 is released. The sidewalls 16 are swung open and separated. The cross-members 44 are swung up and each sidewall 16 is connected by attaching the cross-members 44 to a pressure sleeve 46. The body 20 is then draped over the frame 14.

The body 20 can be made of any suitable lightweight and flexible material such as a transparent plastic so that the patient 12 can see out and the medical personnel can see into the chamber 10. The material is flexible so that it can deform to different size patients on the lower edge 28 of the front sidewall 16. The front sidewall 16 of the body 20 can have a formed cutout to allow the patient's head 22 and even part of their torso extend through. A sealing skirt can be draped in this area to improve the negative pressure capabilities of the chamber 10 and be coupled to the front sidewall 16.

Various access holes 26 can be provided through the sidewalls 16 and/or the curved center portion 18. As illustrated in the FIGURES, two access holes 26 are provided on the rear sidewall 16, one on the front sidewall 16, and at least one access hole 26 on the curved center portion 18 proximate to either the left or right side. To make the chamber 10 ambidextrous, the access holes 26 that are to be used for insertion of arms by the medical personnel can be formed in a mirror image or in other places. By placing other access holes 26, a second medical personnel can assist with intubation of the patient 12. In addition, access holes 26 can provide mechanisms for allowing passage of the air on a regulated basis into the chamber 10, as well as smaller access holes 26 that can include fittings or other mechanisms to attach the chamber 10 to a vacuum, such as the wall vacuum line in a hospital room.

Figure 5:
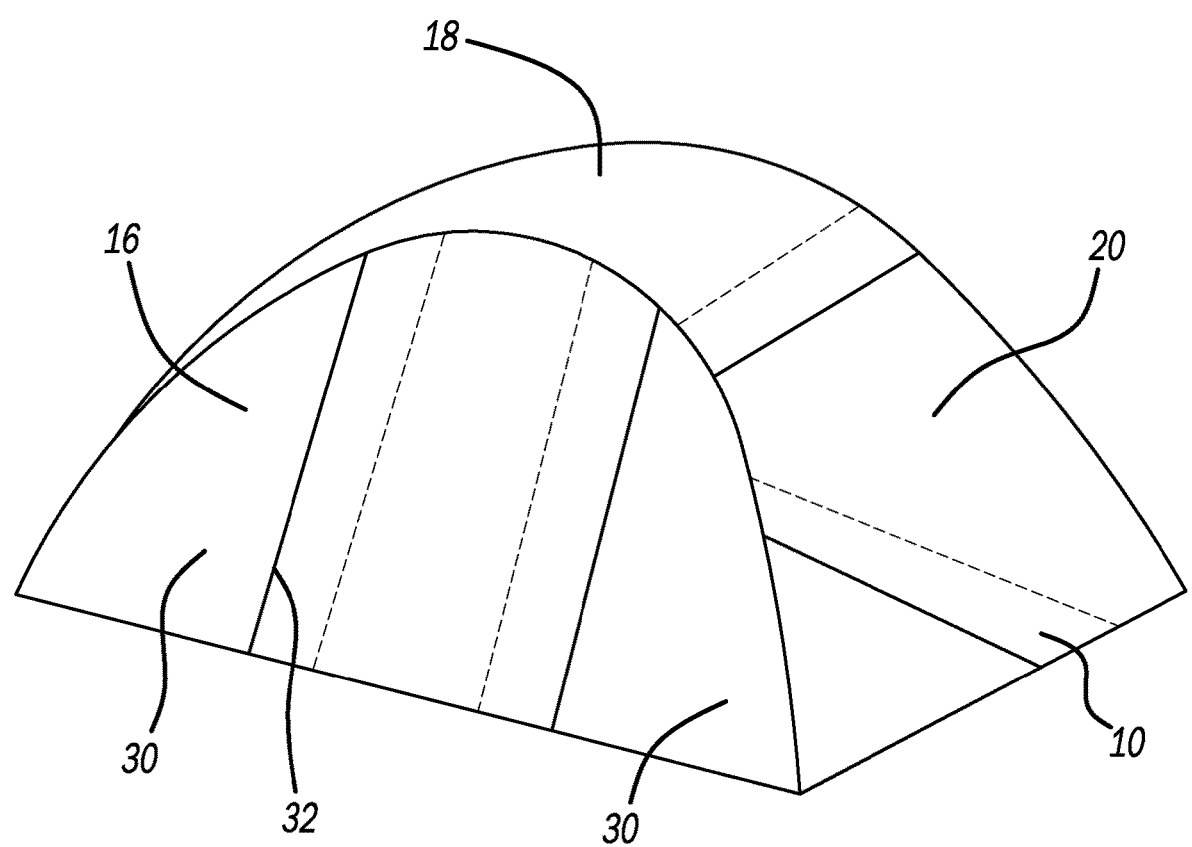
FIG. 5 is a perspective view of the chamber.

The access holes 26 can be replaced or supplemented with simply overlapping sheets 30 of flexible plastic, as illustrated in FIG. 5 along a seam 32, which allows the healthcare provider to stick their arms through the sidewalls 16 but be able to slide their arms up and down, which allows for better adjustability for the health care provider's height. The seam 32 is illustrated with the one edge on the outside of the chamber 10 with a solid line and the edge of the other overlapping sheet 30 ending at the dotted line on the inside of the chamber 10. More specifically, instead of individual holes cut through the chamber 10, the chamber 10 is formed with multiple overlapping sheets of material 30, and the health care provider slides their arm between the sheets 30 to allow access to the chamber 10. Of course, this can cause an increase of air flow versus the individual hole design, however this can be easily adjusted by increasing the capability of the system that causes the vacuum inside of the chamber 10. As illustrated, a variety of other sizes, shapes, and styles of the overlapping seams 32 can be used to best adjust for the access to the patient 12 and the actions required to intubate the patient 12. In fact, it can be desirable to have many more overlapping seams 32 than strictly necessary as this will allow doctors to easily access their patient 12 using their desired positioning relative to the patient 12, as if the chamber 10 was not over the patient 12.

Figure 4:
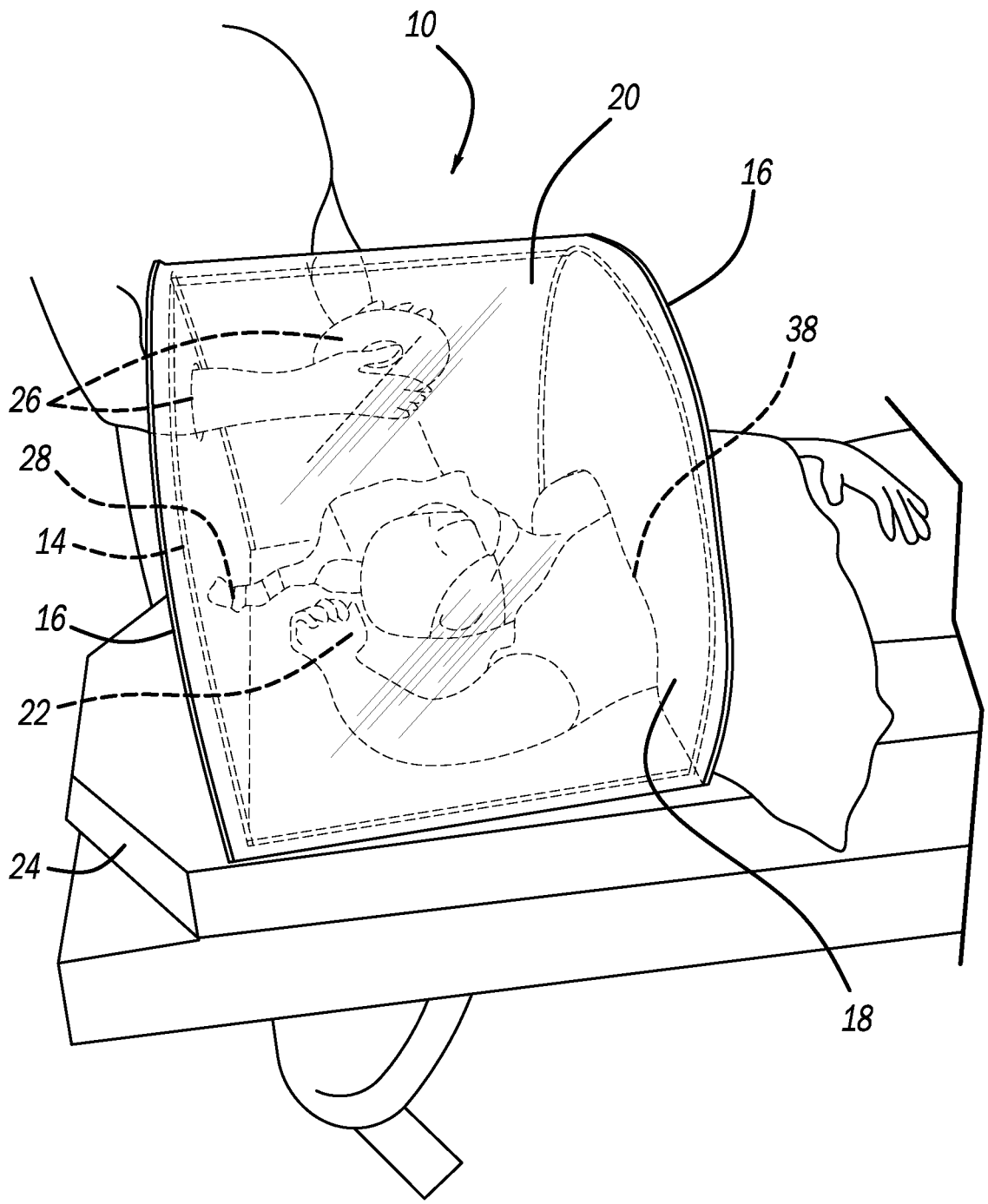
FIG. 4 is a left side perspective picture of the chamber in use.

A negative pressure can be provided within the chamber or shield 10, such as by connecting the chamber 10 to wall vacuum to evacuate any droplets containing COVID-19 or another infectious disease before they can reach the attending medical personnel. In FIG. 4, a vacuum line 28 can be seen running to and passing through the rear sidewall 16. While this could pass through to another element, it can also be just connected to the rear sidewall 16. By sizing the chamber 10 to fit within the standard hospital bed 24, the chamber 10 can be placed over a patient 12 without the patient 12 having to leave the bed 24, and the bed 24 can be used as the lower wall of the chamber 10 to create a cavity inside the chamber 10 with negative pressure. In addition, the access holes 26 can have sealing engagements 34 that minimize air flow through them when no arm is inserted, but also allow an arm to be inserted through while maintaining the sealing engagement. The sealing engagement 34 does not have to be perfect and in fact it is more important to allow freedom of movement for the medical personnel but needs to be sealing enough to allow creation of the negative pressure in the chamber 10. The illustrated sealing engagements 34 can be made from a flexible material that substantially closes when no arm is inserted and allows easy insertion of an arm may be configured in a variety of other shapes, sizes or configurations and can be made from a variety of materials. One of the access holes 26 can include a vent control 36 which can allow adjustment of the level of negative pressure in the chamber 10 easily while working on the patient, without having to adjust it at the wall. As illustrated in FIGS. 2 and 3, the access hole 26 can include an adjustable spinner vent 36, that one can rotate to various levels of open and rotate back closed. The access holes 26 can require a small frame around the access holes 26 or some other rigid element to which the sealing engagements 34 can attach. With negative pressure present, there needs to be some ventilation in the chamber 10 to allow outside air inside the chamber 10 to prevent the chamber 10 from collapsing, as well as allow clean air to be accessed by the patient but preventing contamination from the patient to outside.

While a ventilation line for the patient 12 once intubated can pass through the body 20 of the chamber 10, it just as easily can pass under the body 20 of the chamber 10 (including the center portion 18), which allows easy removal by lifting it off the patient 12 without having to disconnect the chamber 10. This is a major improvement over having a system with a lower wall or forced connections through the walls, which would require major effort and time to remove from a patient once intubated. More specifically, in practice, when a patient 12 is ready to be intubated, the chamber 10 can be dropped over the patient, a vacuum line arranged underneath, with the medical personnel sticking their arms through the holes and ready to intubate. The medical devices needed for intubation can be laid by the patient's head 22 before placing the chamber 10 over the patient's head 22.

In addition to connecting to the hospital vacuum lines, the chamber 10 can be provided with other types of connections that allow it to be attached to a portable vacuum, such as a HEPA vacuum for the chamber 10 to be portable and allow for field use outside of a hospital. Furthermore, a viral filter unit, powered can be included and directly interfaced with the chamber 10 to allow for a single contained unit to make the negative pressure (further described below). The fan can be located externally and pull air through a HEPA or Viral filter located within or attached to the chamber 10. It can also be located on the inner surface of the chamber 10, such as being directly coupled to the supporting frame 14, although for ease of use and to minimize size of the unit, while keeping sufficient space in the chamber 10, it is believed that any additional attachments would be better suited to be located on the outer surface of the chamber 10.

The body 20 of the chamber 10 can be coated with an antiviral or antibacterial surface coating but can easily be cleaned by simply flipping over the chamber 10. The chamber 10 can be disposable and replaceable, or just the outer plastic body 20 can be replaceable, similar to the way hospitals replace the paper bed coverings in examining rooms, with the outer plastic body 20 easily uncoupling or being removed from the frame 14 and dropping a new plastic body 20 over the frame.

Figure 15A:
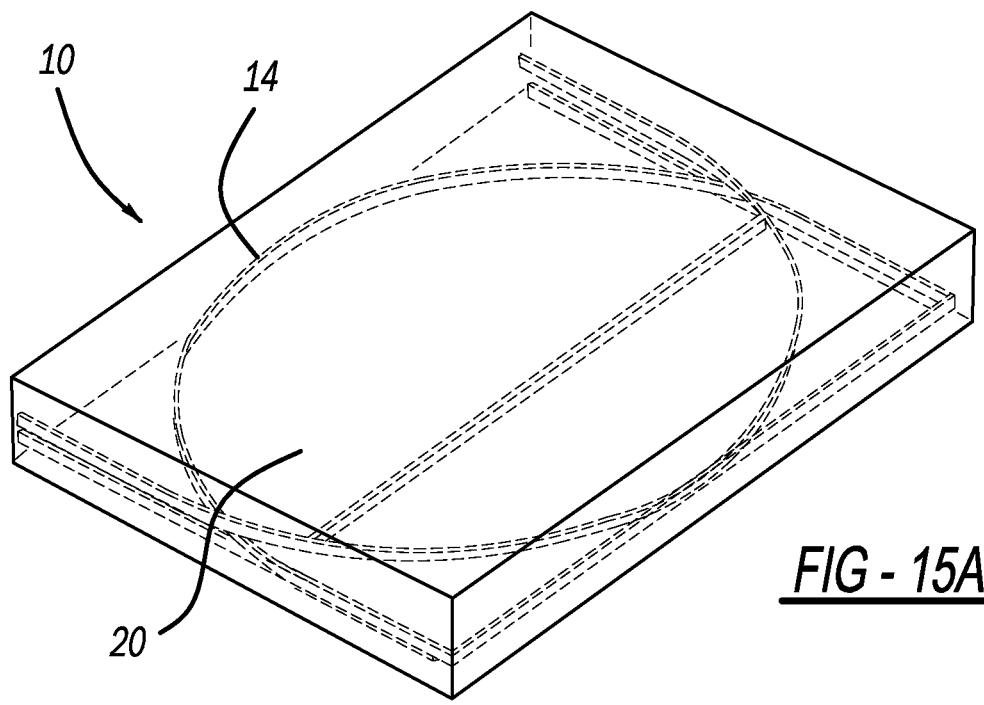
FIG. 15A is a top perspective view of a folded chamber.
Figure 15B:
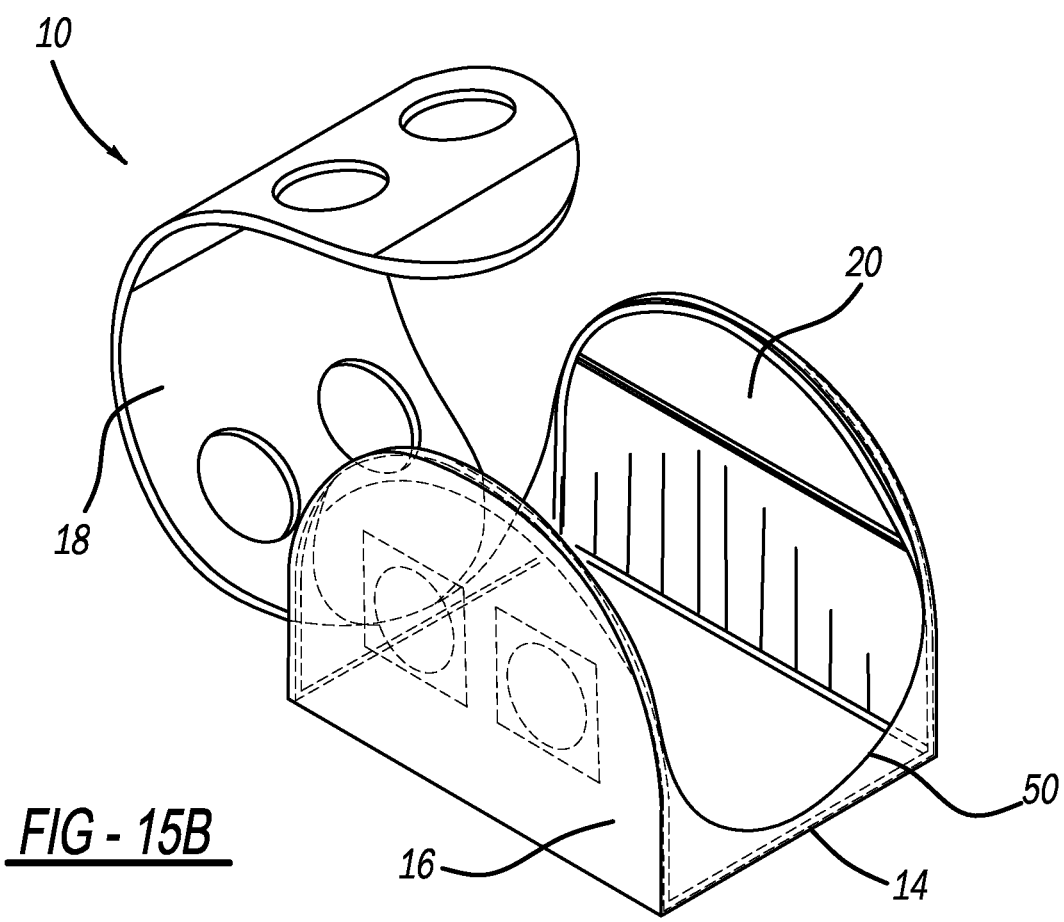
FIG. 15B is a side perspective view of attaching a curved center portion with zippers.
Figure 15C:
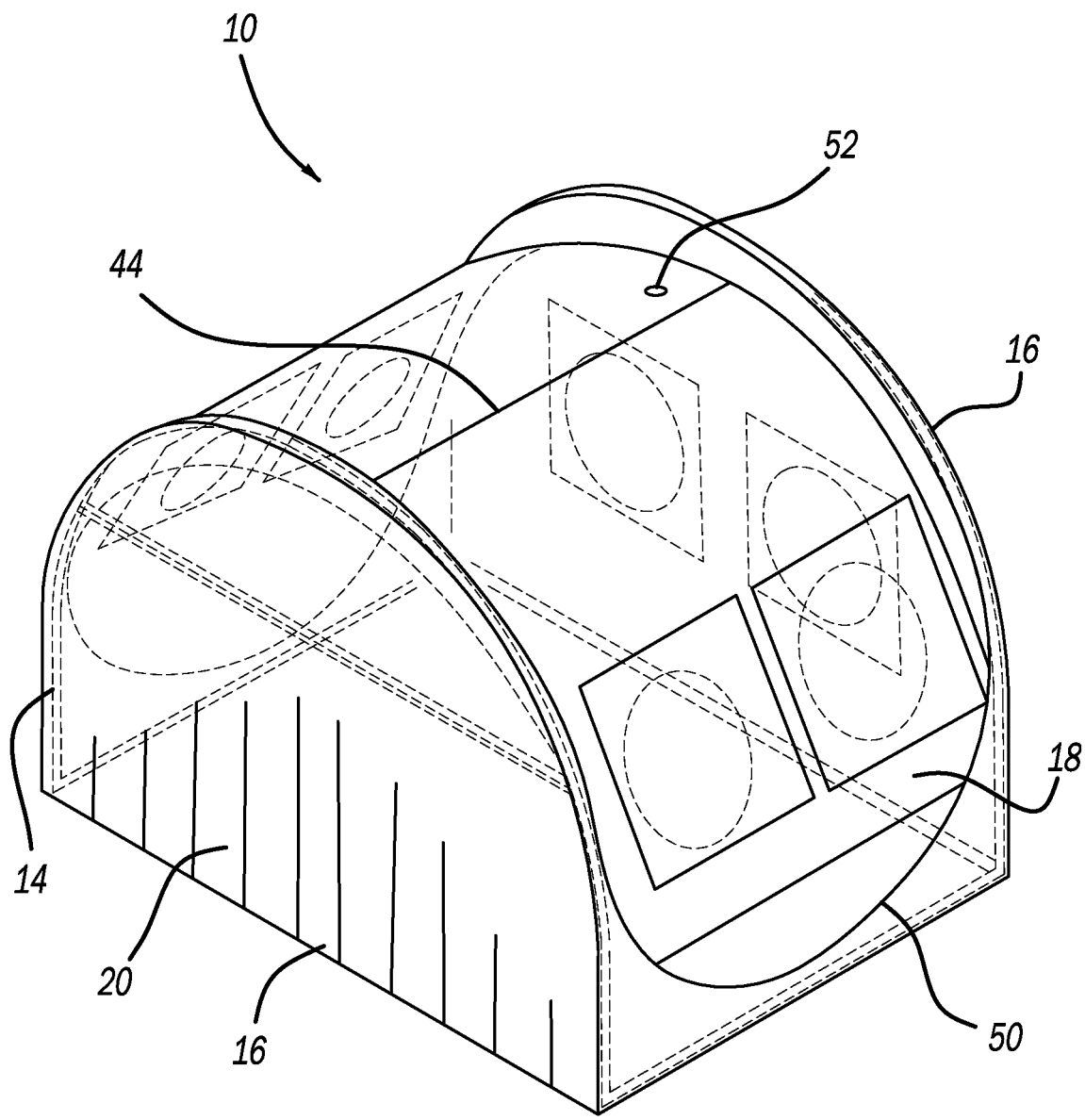
FIG. 15C is a side perspective view of a chamber assembled with zippers.

The body 20 can include zippers 50 operatively integrated within the material of body 20 (such as by RF welding) for easy assembly and disassembly. For example, as shown in FIG. 14 and FIGS. 15A-15C, zippers 50 can be included such that a portion of the curved center portion 18 of the body 20 is attachable to the sidewalls 16 of the body 20. When zipped, the curved center portion 18 adds stability and rigidity to the structure of the chamber 10 and fully encloses the chamber 10. In this design, portions of the frame 14 can also be operatively integrated by RF welding into the body 20 (i.e., sidewall 16 portions can be RF welded into the body 20, and cross-members 44 can be RF welded into the curved center portion 18 of the body 20). A negative pressure port 52 is included operatively integrated within the body 20 at any suitable location to allow the chamber 10 to be hooked up to a vacuum source. The negative pressure port 52 can be a hose barb that is RF welded onto the curved center portion 18 of the body 20, and a negative pressure hose can be hooked onto the hose barb. In FIGS. 15A-15C, assembly of the chamber 10 is shown. In FIG. 15A, during transportation or when not in use, the body 20 can be unzipped and rolled up. The curved center portion 18 can be rolled up or folded in the center of the chamber 10. Sidewalls 16 are folded down over the rolled up curved center portion 18. FIG. 15B shows the body 20 being zipped up (i.e., the curved center portion 18 being attached to the sidewalls 16). FIG. 15C shows the chamber 10 fully assembled and zipped.

Figure 16:
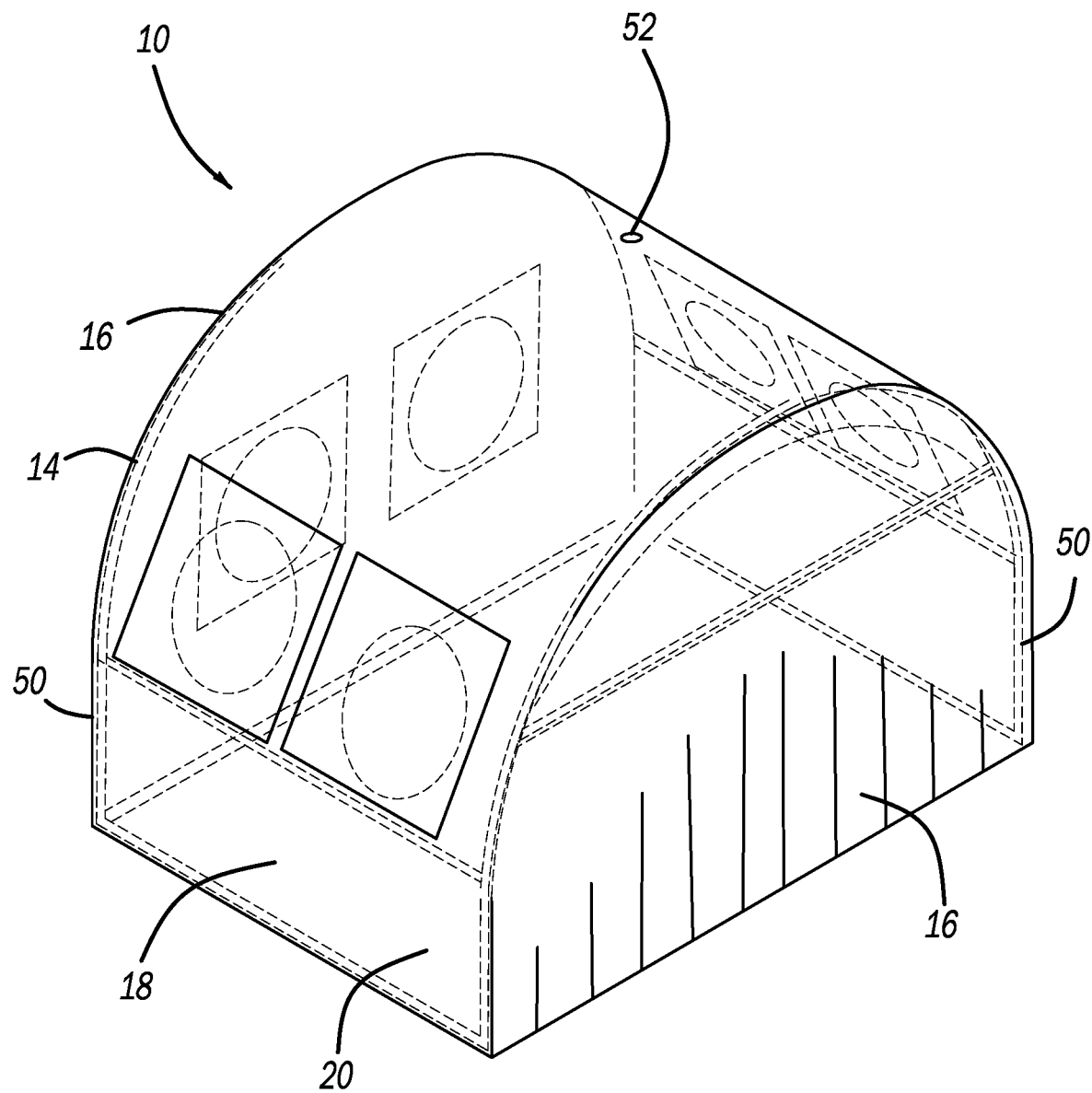
FIG. 16 is a side perspective view of a chamber assembled with zippers along sidewalls.
Figure 17:
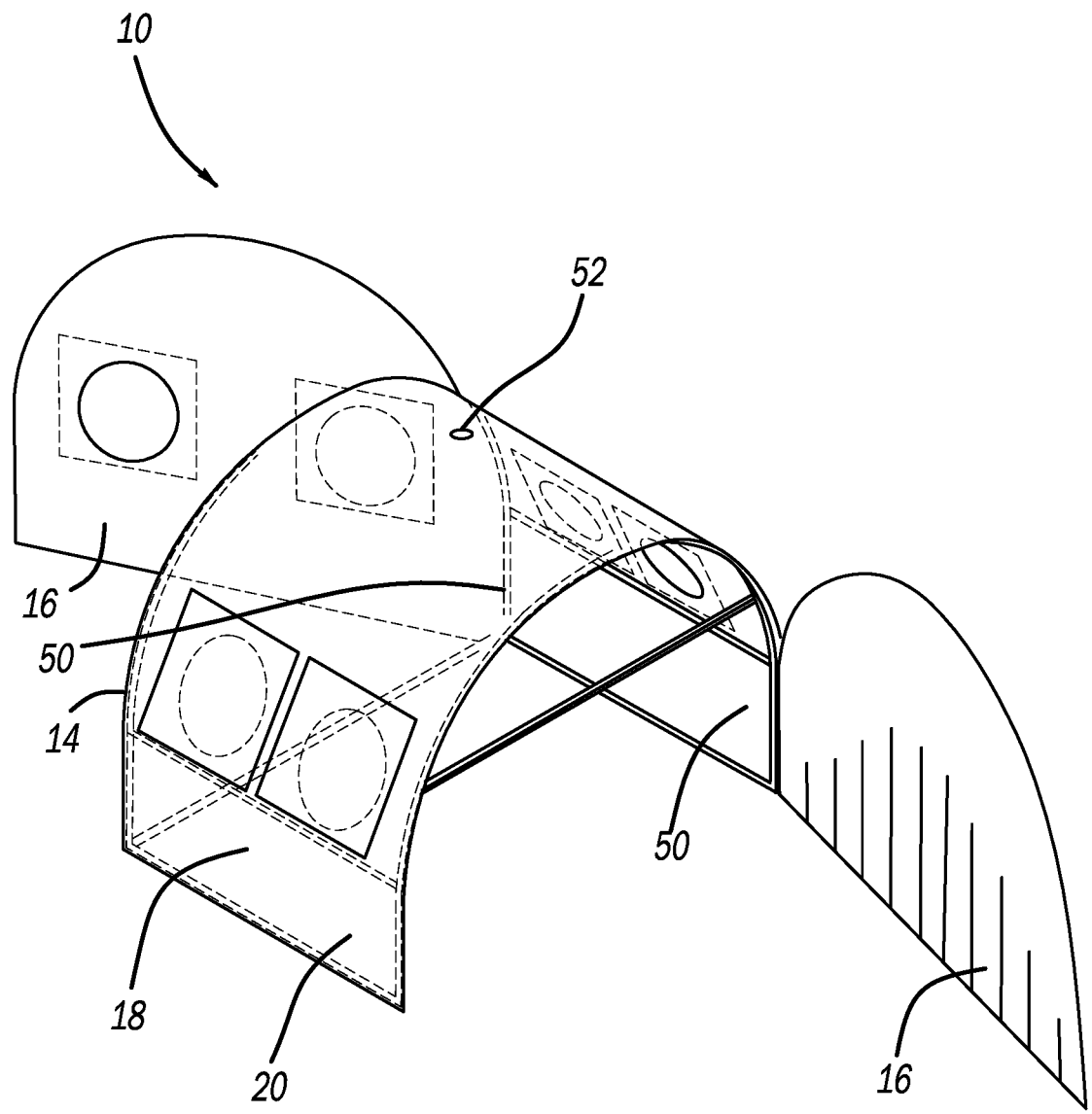
FIG. 17 is a side perspective view of a chamber with sidewalls being zipped onto a center curved portion.
Figure 18:
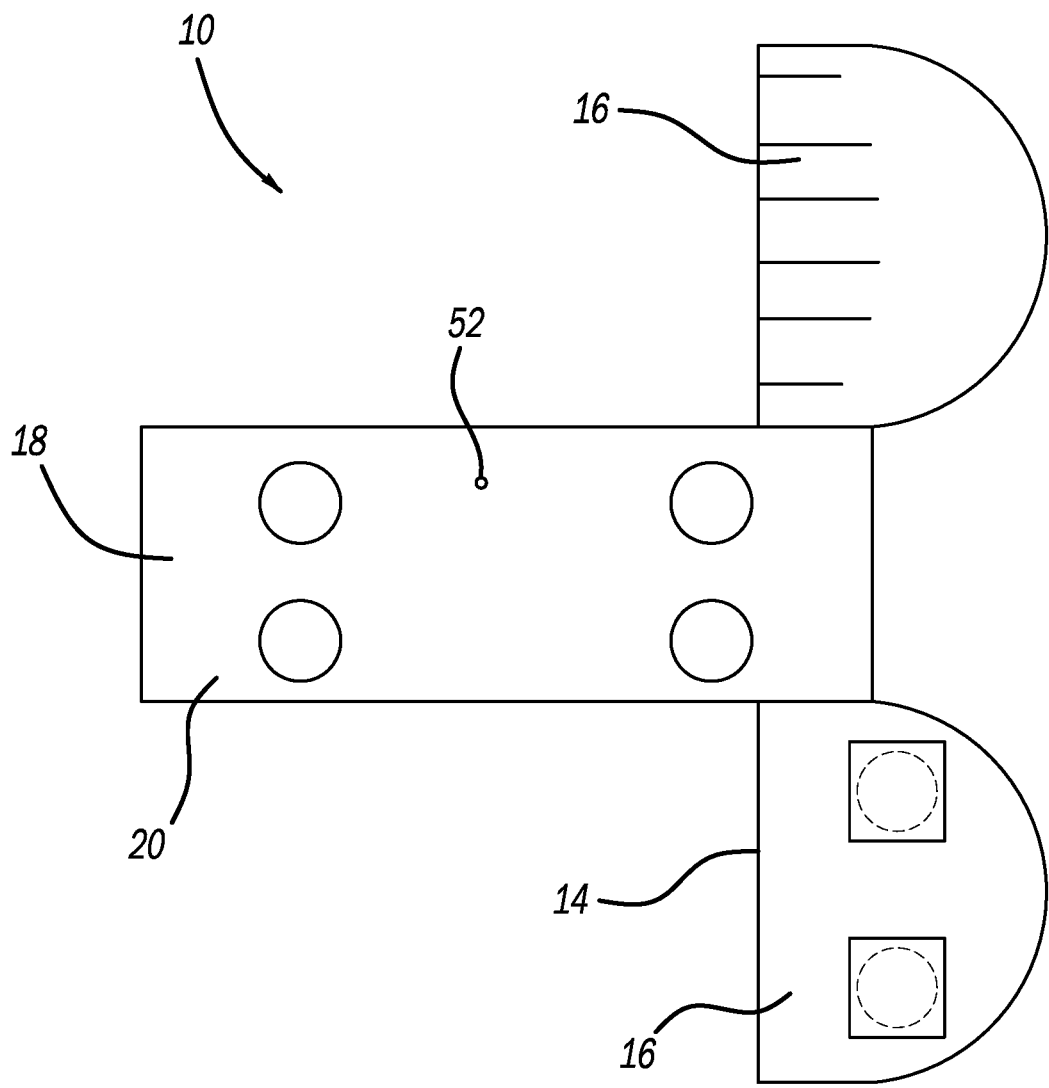
FIG. 18 is a side perspective view of a chamber unzipped.

In another example, shown in FIGS. 16-18, sidewalls 16 can be fully zipped or unzipped from the curved center portion 18 with zippers 50 (i.e., the zippers 50 span the curvature of the chamber 10 and the entire curved center portion 18 instead of just a portion of the curved center portion 18). When the sidewalls 16 are zipped to the curved center portion 18, shown in FIG. 17, they form the chamber 10. The negative pressure port 52 can be included as described above. The frame 14 can be RF welded within the sidewalls 16 and curved center portion 18 as above. The frame 14 provides support to the chamber 10 when it is fully zipped. When the chamber 10 is unzipped, as shown in FIG. 18, it lays flat and the sidewalls 16 can be folded into the curved center portion 18 for storage or transport.

Figure 19A:
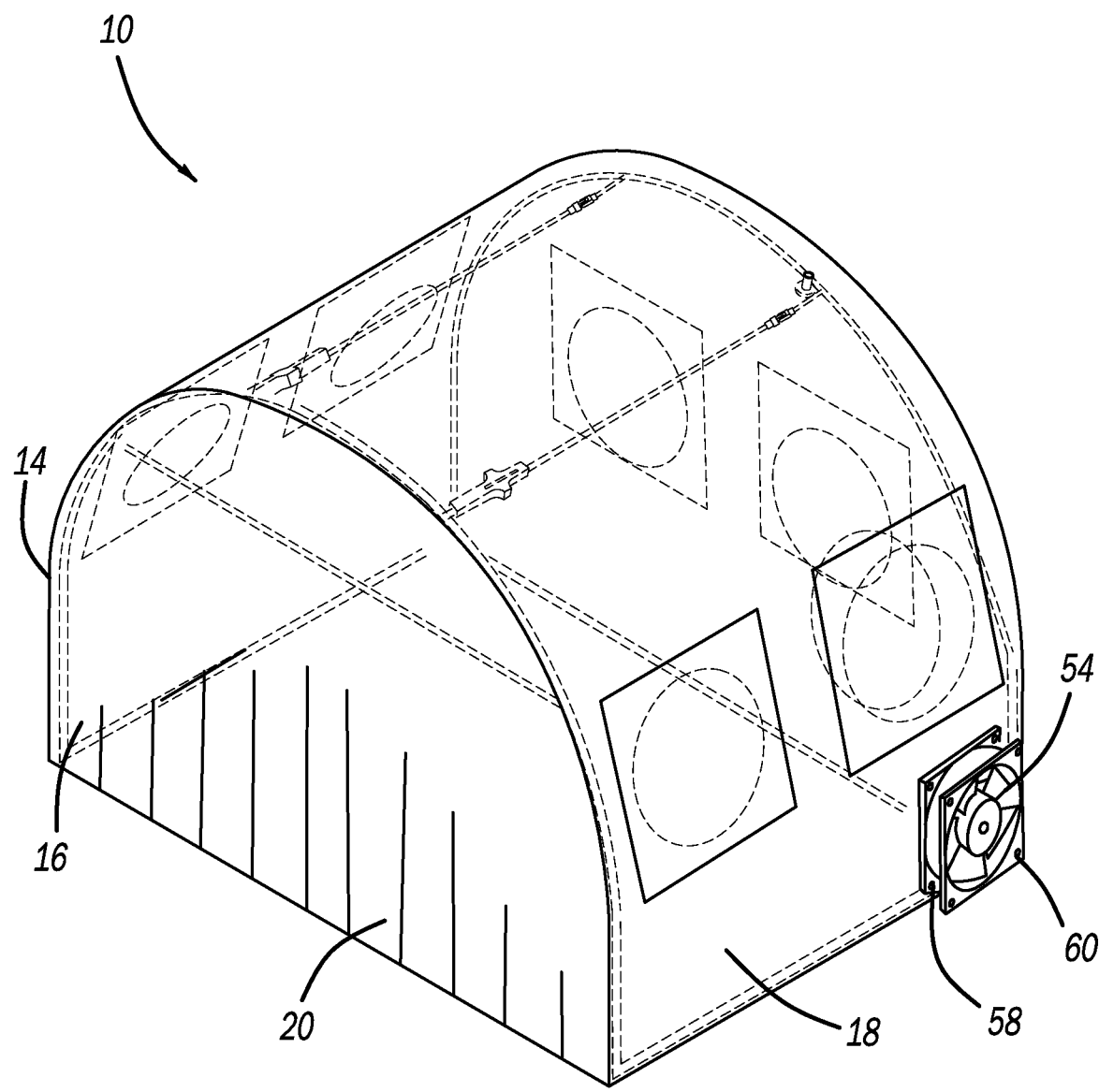
FIG. 19A is a side perspective view of a self-contained negative pressure aerosol chamber.
Figure 19B:
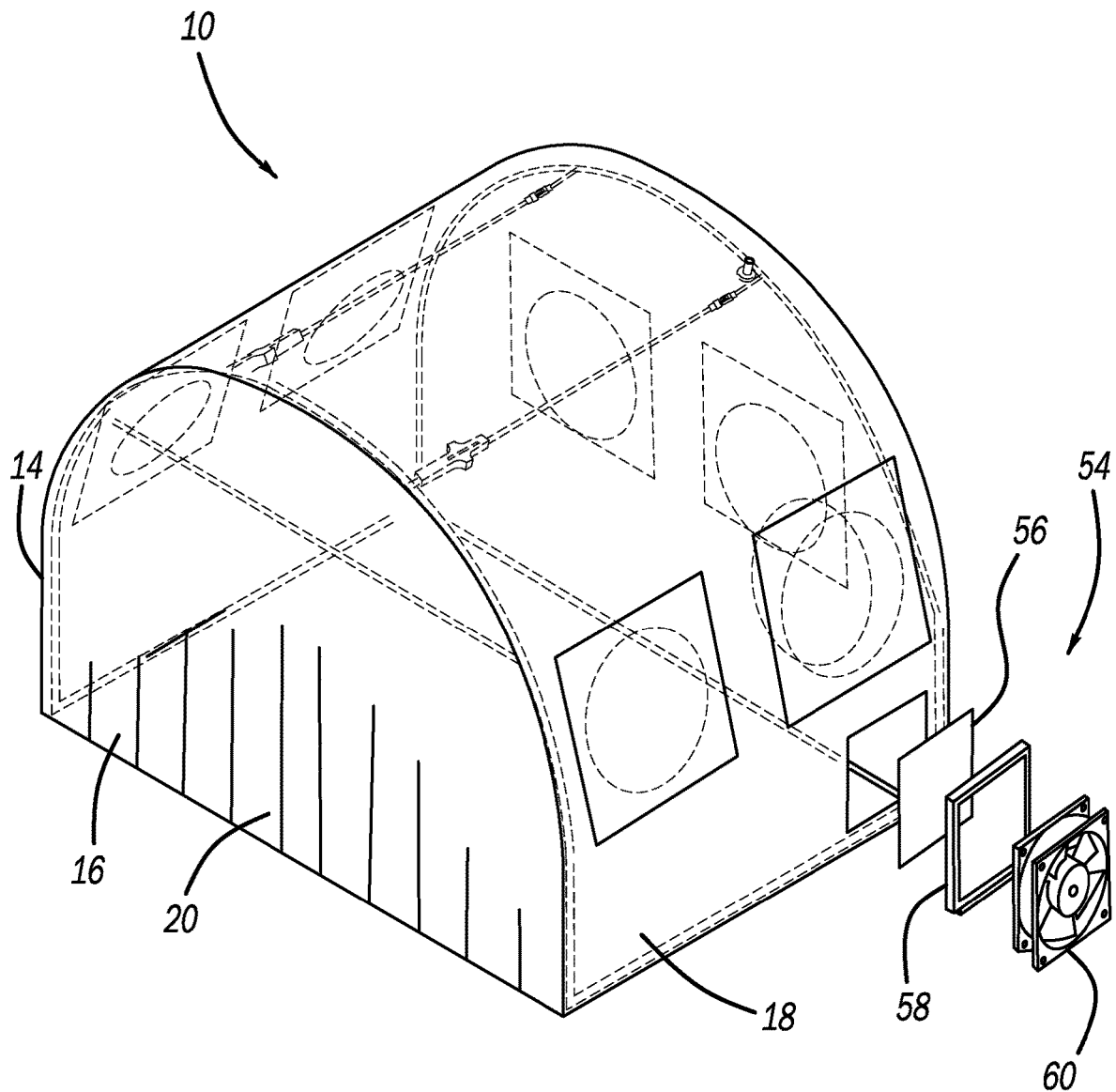
FIG. 19B is a side perspective and exploded view of the chamber with a HEPA filter and negative pressure source.
Figure 19C:
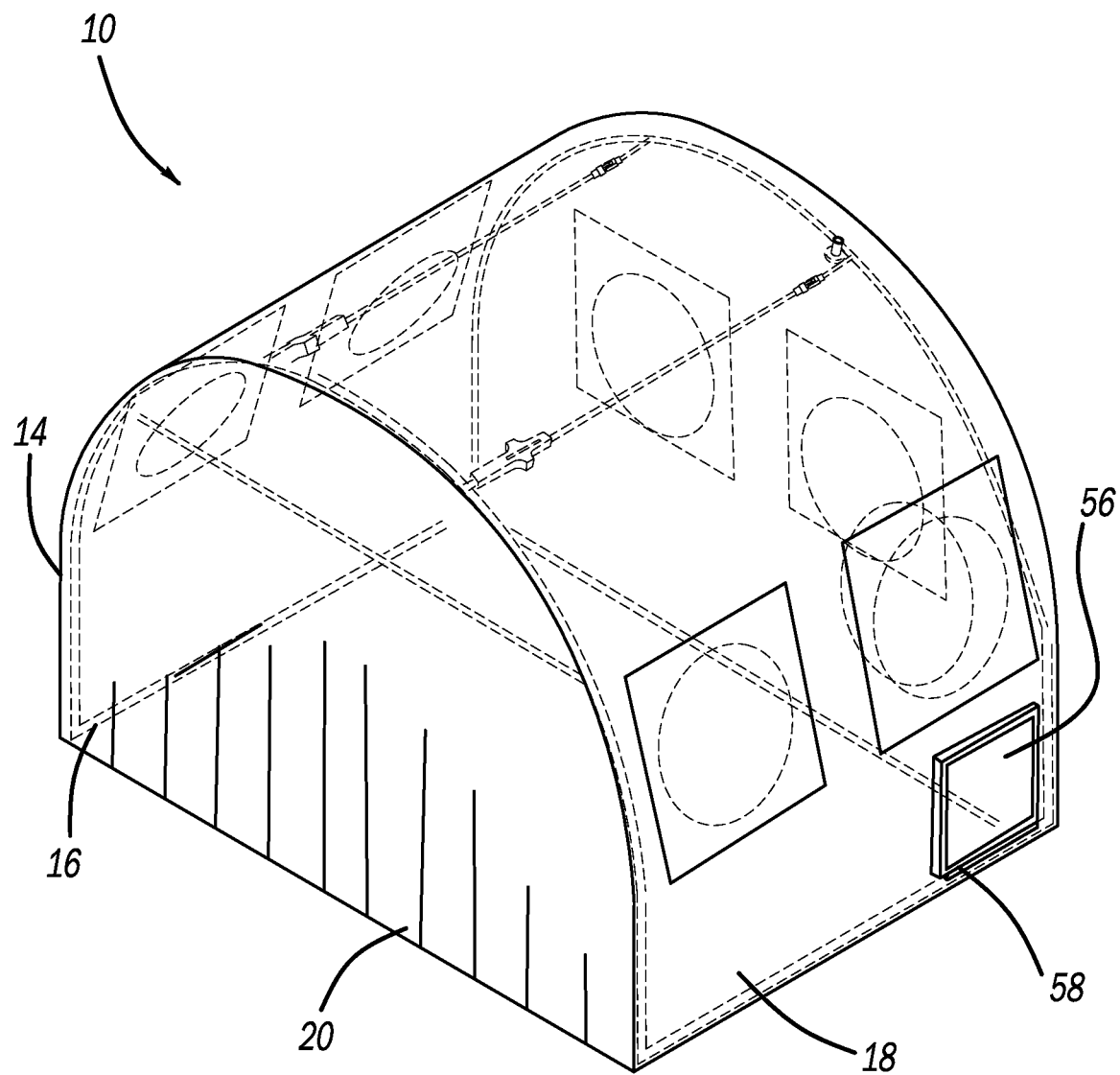
FIG. 19C is a side perspective view of the chamber with a HEPA filter and fan housing.

The chamber 10 can further include a negative pressure mechanism 54, shown in FIGS. 19A-19C. In this design, instead of using a portable suction machine or a wall vacuum system to generate negative pressure within the chamber 10, the negative pressure mechanism 54 is integrated into the chamber 10 itself. As shown in FIGS. 19B-19C, the negative pressure mechanism 54 includes a HEPA filter 56 sealed onto the body 20, for example in a portion of the curved center portion 18 as shown in FIG. 19A. A plastic housing 58 that uses J-clips 62 (or any other suitable attachment mechanism) is welded onto the body 20 surrounding the HEPA filter 56. A high CFM fan 60 clips into the J-clips 62 of the housing 58. The high CFM fan 60 is battery powered and generates airflow through the HEPA filter 56, thus pulling dangerous aerosols out of the chamber 10. The aerosols are trapped within the fibers of the HEPA filter 26 material providing purified air to a room. The high CFM fan 60 can be easily removed from the housing 58 and moved to and attached to another chamber 10.

The present invention provides for a method of using a chamber 10 of to perform a medical procedure on a patient 12 releasing virus, bacteria, or other contaminants, by placing the chamber 10 over a patient's head 22 on a bed 24, wherein the chamber 10 includes a frame 14 forming and supporting two sidewalls 16 and a curved center portion 18 extending between the sidewalls 16 of a transparent body 20, wherein the body 20 includes at least one access hole 26, and wherein the one of the sidewalls 16 deforms around the patient's body, providing negative pressure within the chamber 10, and medical personnel providing intubation to the patient 12 through the at least one access hole 26 in the body 20 of the chamber 10 while capturing and exhausting any of the virus, bacteria, or other contaminants released by the patient during the medical procedure. In other words, the chamber 10 allows for preventing infectious disease droplets from exiting the chamber 10 to medical personnel. The method can further include assembling the chamber 10 by connecting cross-members and draping body 20 over the frame 14 as described above or zipping the sidewalls 16 and curved center portion 18 together with the frame 14 integrated within the body 20 as described above. The method can further include disassembling the chamber 10 by disconnecting cross-members and removing body 20 from the frame 14 as described above or unzipping the sidewalls 16 and curved center portion 18 together with the frame 14 integrated within the body 20 as described above. Negative pressure can be provided by attaching a vacuum line 28 to the chamber 10 or by using the negative pressure mechanism 54.

The terminology used herein is for the purpose of describing particular example aspects only and is not intended to be limiting. As used herein, the singular forms "a," "an," and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

When an element or feature is referred to as being "on," "engaged to," "connected to," "coupled to" "operably connected to" or "in operable communication with" another element or feature, it may be directly on, engaged, connected, or coupled to the other element or layer, or intervening elements or features may be present. In contrast, when an element is referred to as being "directly on," "directly engaged to," "directly connected to," or "directly coupled to" another element or feature, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another region, layer, or section. Terms such as "first," "second," and other numerical terms when used herein do not imply a sequence or order unless clearly and expressly indicated by the context. Thus, a first element, component, region, layer, or section discussed below could be termed a second element, component, region, layer, or section without departing from the teachings of the example embodiments.

For purposes of description herein, the terms "upper," "lower," "right," "left," "rear," "front," "vertical," "horizontal," and derivatives thereof shall relate to the invention as oriented in the FIGS. However, it is to be understood that the present disclosure may assume various alternative orientations and step sequences, except where expressly specified to the contrary. It is also to be understood that the specific devices and processes illustrated in the attached drawings and described in the following specification are exemplary aspects of the inventive concepts defined in the appended claims. Hence, specific dimensions and other physical characteristics relating to the aspects disclosed herein are not to be considered as limiting, unless the claims expressly state otherwise.

Throughout this application, various publications, including United States patents, are referenced by author and year and patents by number. Full citations for the publications are listed below. The disclosures of these publications and patents in their entireties are hereby incorporated by reference into this application in order to more fully describe the state of the art to which this invention pertains.

The invention has been described in an illustrative manner, and it is to be understood that the terminology, which has been used is intended to be in the nature of words of description rather than of limitation.

Obviously, many modifications and variations of the present invention are possible in light of the above teachings. It is, therefore, to be understood that within the scope of the appended claims, the invention can be practiced otherwise than as specifically described.

What is claimed is:

1. A chamber for placement over a patient while allowing medical personnel to perform a medical procedure on the patient releasing virus, bacteria, or other contaminants, consisting of:
   a frame forming and supporting two sidewalls and a curved center portion extending between said sidewalls of a transparent body made of only a flexible plastic, wherein said curved center portion is shaped in an arch, wherein said body includes at least one access hole, and wherein said chamber is configured to surround said patient's head and one of said sidewalls is configured to deform around said patient's body in order to capture and exhaust any of said virus, bacteria, or other contaminants released by said patient during said medical procedure through negative pressure.

2. The chamber of claim 1, wherein said chamber is sized to fit on a hospital bed.

3. The chamber of claim 1, wherein said frame is made of a material chosen from the group consisting of plastic and metal.

4. The chamber of claim 1, wherein said frame includes at least one hinge along a base and at least one cross-member connecting said two sidewalls.

5. The chamber of claim 4, wherein said at least one cross-member is releasably secured to said sidewall and includes a pressure sleeve at a first end and a hinge at a second end.

6. The chamber of claim 1, wherein said body and frame are attached in a manner chosen from the group consisting of said body being draped over said frame and said frame being operatively integrated in said body.

7. The chamber of claim 1, wherein said frame is foldable.

8. The chamber of claim 7, further including a securing mechanism for securing said frame when folded.

9. The chamber of claim 1, wherein a rear sidewall includes two access holes, a front sidewall includes one access hole, and said curved center portion includes two access holes.

10. The chamber of claim 9, further including overlapping sheets of flexible plastic situated over said access holes.

11. The chamber of claim 9, wherein said access holes include sealing engagements for minimizing air flow when no arm is inserted therein.

12. The chamber of claim 9, wherein one said access hole includes a vent control for adjusting a level of negative pressure in said chamber.

13. The chamber of claim 1, wherein said chamber is configured to receive negative pressure by a wall vacuum.

14. The chamber of claim 1, wherein negative pressure is provided to said chamber with a negative pressure mechanism including a HEPA filter operatively sealed onto said body, a housing being welded onto said body, said housing including J-clips and surrounding said HEPA filter, and a fan being clipped into said J-clips.

15. The chamber of claim 1, wherein said chamber is disposable.

16. The chamber of claim 1, wherein said body includes zippers operatively integrated therein and said two sidewalls and curved center portion are attachable through said zippers.

17. A method of using a chamber of to perform a medical procedure on a patient releasing virus, bacteria, or other contaminants, including the steps of:
   placing a chamber over a patient's head on a bed, wherein the chamber consists of a frame forming and supporting two sidewalls and a curved center portion extending between the sidewalls of a transparent body made of only a flexible plastic, wherein the curved center portion is shaped in an arch, wherein the body includes at least one access hole, and wherein the one of the sidewalls deforms around the patient's body;
   providing negative pressure within the chamber; and
   medical personnel providing intubation to the patient through the at least one access hole in the body of the chamber while capturing and exhausting any of the virus, bacteria, or other contaminants released by the patient during the medical procedure.

18. The method of claim 17, further including before said placing step, the step of assembling the chamber by a method chosen from the group consisting of 1) connecting cross-members of the frame and draping the body over the frame, 2) and zipping the sidewalls and curved center portion together.

19. The method of claim 17, further including the steps of disassembling the chamber by a method chosen from the group consisting of 1) disconnecting cross-members of the frame and removing the body from the frame, and 2) unzipping the sidewalls and curved center portion, and folding the frame.

20. The method of claim 17, wherein said providing negative pressure step is further defined as a step chosen from the group consisting of 1) using a wall vacuum connected to the chamber and 2) using a negative pressure mechanism including a HEPA filter operatively sealed onto the body, a housing being welded onto the body, the housing including J-clips and surrounding the HEPA filter, and a fan being clipped into the J-clips.

* * * * *